United States Patent
Zuo et al.

(10) Patent No.: US 9,606,260 B2
(45) Date of Patent: Mar. 28, 2017

(54) OIL BASED DRILLING MUD FILTRATE CONTAMINATION MONITORING USING GAS TO OIL RATIO

(71) Applicant: Schlumberger Technology Corporation, Sugar Land, TX (US)

(72) Inventors: Youxiang Zuo, Sugar Land, TX (US); Adriaan Gisolf, Houston, TX (US); Anthony Smits, Yokohama (JP); Oliver C. Mullins, Ridgefield, CT (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 984 days.

(21) Appl. No.: 13/865,839

(22) Filed: Apr. 18, 2013

(65) Prior Publication Data
US 2014/0316705 A1    Oct. 23, 2014

(51) Int. Cl.
*E21B 49/08* (2006.01)
*G01V 8/10* (2006.01)
*G01N 33/28* (2006.01)

(52) U.S. Cl.
CPC .......... *G01V 8/10* (2013.01); *G01N 33/2823* (2013.01); *E21B 49/088* (2013.01)

(58) Field of Classification Search
CPC combination set(s) only.
See application file for complete search history.

(56) References Cited

U.S. PATENT DOCUMENTS

| | | | |
|---|---|---|---|
| 5,635,631 A * | 6/1997 | Yesudas et al. | 73/61.46 |
| 6,956,204 B2 | 10/2005 | Dong et al. | |
| 7,305,306 B2 * | 12/2007 | Venkataramanan et al. | 702/9 |
| 7,920,970 B2 | 4/2011 | Zuo et al. | |
| 2003/0006768 A1 | 1/2003 | Kleinberg et al. | |
| 2004/0193375 A1 | 9/2004 | Dong et al. | |
| 2006/0226699 A1 | 10/2006 | Betancourt et al. | |
| 2006/0250130 A1 | 11/2006 | Akkurt et al. | |
| 2009/0289628 A1 | 11/2009 | Cao Minh | |
| 2012/0232859 A1 * | 9/2012 | Pomerantz et al. | 703/2 |

OTHER PUBLICATIONS

International Search Report and Written Opinion issued in PCT/US2014/034188 on Aug. 12, 2014, 13 pages.
U.S. Appl. No. 13/721,981, filed Dec. 20, 2012.
Zuo, et al., "A New Method for OBM Decontamination in Downhole Fluid Analysis", IPTC 16524—6th International Petroleum Technology Conference, Beijing, China, Mar. 26-28, 2013.

* cited by examiner

*Primary Examiner* — Huan Tran
(74) *Attorney, Agent, or Firm* — Michael Dae (57) ABSTRACT

A method for monitoring oil based mud filtrate contamination is provided including steps of analytically dividing a fluid stream into two parts, determining a gas/oil ratio for a native fluid determining an apparent gas/oil ratio for the contaminated fluid and determining on a volume fraction, an oil based contamination level based upon the gas/oil ratio for the native fluid and the apparent gas/oil ratio for the contaminated fluid.

16 Claims, 6 Drawing Sheets

OIL BASED DRILLING MUD FILTRATE CONTAMINATION MONITORING USING GAS TO OIL RATIO

CROSS-REFERENCE TO RELATED APPLICATIONS

None.

FIELD OF THE INVENTION

Aspects relate to the field of oil well services. More specifically, aspects relate to oil based drilling mud filtrate contamination monitoring.

BACKGROUND INFORMATION

Oil based drilling mud (OBM) filtrate contamination monitoring (OCM) is one of the biggest challenges in downhole fluid analysis. Conventional systems and algorithms are not capable of providing adequate results for OBM contamination monitoring, particularly with focused sampling interface modules. Accurate and quantitative OBM contamination measurement is a key enabler of quality sampling and quality downhole fluid analysis (DFA). New algorithms are highly demanded for this purpose.

Conventional systems do not disclose or suggest any capability that gas/oil ratios may be used in oil based mud filtrate contamination monitoring quantitatively. Previous attempts at developing a relationship have failed as conventional fluid analyzers display a negative gas/oil ratio in Oil Based mud filtrate. This limits its use in quantifying Oil Based mud contamination. Extrapolating contamination free gas/oil ratios determined by asymptotic fitting methods does not work, especially for focused probes and/or new developed probes and packers.

SUMMARY

In one example embodiment, a method for monitoring OBM contamination, is disclosed, comprising analytically dividing a fluid stream into two parts, determining a gas/oil ratio for a native (or OBM filtrate contamination free) fluid, determining an apparent gas/oil ratio for the native fluid, and determining on a volume fraction, an oil based mud filtrate contamination level based upon the gas/oil ratio for the native fluid and the apparent gas/oil ratio for the native fluid.

A novel procedure is provided for oil based mud filtrate contamination monitoring and determination of oil based mud filtrate contamination level. Based on the definition of gas/oil ratio, a simple formula is developed to relate oil based mud filtrate contamination level in volume fraction in stock tank oil (STO) to apparent gas/oil ratio which is measured by downhole fluid analysis. The end point for native (contamination free) oil can be determined in different ways using multiple sensors in downhole fluid analysis. Additionally, density itself can be used for oil based mud filtrate contamination monitoring using a mixing rule. When combining the oil based mud contamination level results from gas/oil ratio, density and pressure gradients with those from optical density calculations, confidence is significantly gained in particular when all the results are close. In addition, the oil based mud filtrate contamination monitoring algorithms can be applied not only for individual guard and sampling flowlines but also for combined guard and sampling flowlines. These formulas and algorithms can be used for oil based mud filtrate contamination monitoring in real time and postjob analysis.

DETAILED DESCRIPTION

Through aspects described herein, it is now possible to use the value of gas/oil ratio for oil based mud filtrate contamination monitoring. The oil based mud filtrate contamination monitoring formula is derived from the definition of gas/oil ratio and oil based mud filtrate contamination level in volume fraction on the basis of dead oil (stock tank oil, STO). Confidence is significantly gained using gas/oil ratio as oil based mud filtrate contamination monitoring due to this theoretical base.

Additionally, the new generation of downhole fluid analysis, like in situ fluid analyzer, avoids negative gas/oil ratio (normalizing GOR to zero for dead oil) in the algorithm and the assumption of zero gas/oil ratio for pure oil based mud filtrate is valid.

Contamination free $GOR_0$ for native oil can be determined from different methods, which can gain confidence for the analysis. For example, (1) density derived from pressure gradients and $GOR_0$ from a linear relationship between density and gas/oil ratio measured by downhole fluid analysis; (2) $GOR_0$ from the asymptotic fitting method is also used for reference. The linear relationship between density and gas/oil ratio is confirmed by laboratory and field data.

In an asymptotic fitting method, a new and robust optimization method is provided to reduce arbitrariness in determining the exponential constant of the power function asymptote.

Oil/gas ratio can be measured by downhole fluid analysis based on downhole optical spectra using optical densities at multiple hydrocarbon channels, referred to as apparent gas/oil ratio. In-field practice, apparent gas/oil ratio was used to guide downhole reservoir fluid sampling along with other sensor measurements downhole during cleanup, especially for focused probes and new developed probes and packers. Once apparent gas/oil ratio reaches a stable value with time or/and pumpout volume, one is able to start sampling. Gas/oil ratio can be used as well to determine oil based mud filtrate contamination levels and then for oil based mud filtrate contamination monitoring during cleanup.

It is reasonably assumed that pure oil based mud filtrate has no gas/oil ratio (no gas dissolved in pure oil based mud filtrate) and cannot be vaporized into the gas phase at a single stage flash at standard conditions (the flash process reaches equilibrium). Based on the definition of gas/oil ratio, a simple formula is derived for the first time to relate oil based mud filtrate contamination level in volume fraction in stock tank oil (STO) to gas/oil ratio. Therefore, one endpoint gas/oil ratio for pure oil based mud filtrate is zero, and the other endpoint gas/oil ratio for native oil can be determined in different ways using multiple sensors in downhole fluid analysis.

Using gas/oil ratio and multiple sensors in downhole fluid analysis as oil based mud filtrate contamination monitoring has the following advantages:
1. Using all optical density information in hydrocarbon channels.
2. Large gas/oil ratio contrast (e.g. 0 scf/bbl for oil based mud filtrate and 20-50000 scf/bbl from heavy oil to gas condensate) between pure oil based mud filtrate and native oil.
3. Linear (near linear) relationship between gas/oil ratio and density confirmed from laboratory and field data, which allows to extrapolate gas/oil ratio to native oil based on density from pressure gradients and other methods, which also allows to extrapolate density of pure oil based mud filtrate by setting gas/oil ratio to zero.
4. Engineers may estimate endpoint gas/oil ratio for native oil in a sense from information of nearby wells, nearby downhole fluid analysis stations and the like.
5. Gas/oil ratio and other fluid properties for native oil can be obtained as by-product without oil based mud correction.
6. If the result becomes close by integrating multiple sensor oil based mud filtrate contamination algorithms such as gas/oil ratio, density and optical density, confidence about the answer is significantly gained.
7. Gas/oil ratio cannot be used for oil based mud filtrate contamination monitoring in previous generations of downhole fluid analysis such as optical fluid analyzer, live fluid analyzer and advanced fluid analyzer but a new generation of downhole fluid analysis such as in situ fluid analyzer because the gas/oil ratio algorithm in optical fluid analyzer, live fluid analyzer and advanced fluid analyzer does not normalize gas/oil ratio to zero (negative gas/oil ratio occurs for low gas/oil ratio fluids) at the low end.

For a native live fluid, the single stage flash gas/oil ratio is defined as the ratio of the volume of the flashed gas that comes out of the live fluid solution, to the volume of the flashed oil (also referred to as stock tank oil, STO) at standard conditions (typically 60° F. and 14.7 psia)

$$GOR_0 = \frac{V_{gas}}{V_{oil0}} \quad (1)$$

where $GOR_0$, $V_{gas}$ and $V_{oil0}$ are the gas/oil ratio of the native fluid, the flashed gas volume and the volume of flashed native (oil based mud filtrate contamination free) STO at standard conditions respectively.

The contaminated fluid is divided into two components: the pure oil based mud filtrate and the native fluid. If the reservoir fluid is contaminated by oil based mud filtrate and it is assumed that the oil based mud filtrate exists only in the flashed liquid (oil) phase (i.e., the oil based mud filtrate has no gas/oil ratio), then gas/oil ratio of the contaminated fluid can be expressed as in equation two (2):

$$GOR = \frac{V_{gas}}{V_{STO}} \quad (2)$$

$$= \frac{V_{gas}}{V_{oil0} + V_{obm}}$$

where the total volume of STO ($V_{STO}$) is the summation of the oil based mud filtrate volume ($V_{obm}$) and native STO volume ($V_{oil0}$) at standard conditions. Divided both numerator and denominator by $V_{oil0}$ on the right-hand side, Equation (2) can be rearranged as:

$$GOR = \frac{V_{gas}/V_{oil0}}{(V_{oil0} + V_{obm})/V_{oil0}} \quad (3)$$

$$= \frac{GOR_0}{(V_{oil0} + V_{obm})/V_{oil0}}$$

where the definition of gas/oil ratio, i.e. Equation (1), is used for the native fluid. Furthermore, Equation (3) can be rewritten as:

$$\frac{GOR}{GOR_0} = \frac{V_{oil0}}{(V_{oil0} + V_{obm})} \quad (4)$$

$$= 1 - \frac{V_{obm}}{(V_{oil0} + V_{obm})}$$

$$= 1 - v_{obmSTO}$$

where $v_{obmSTO}$ is the oil based mud filtrate contamination level in volume fraction in stock tank oil (STO) at standard conditions.

Therefore, the oil based mud filtrate contamination level in volume fraction based on STO can be related to gas/oil ratio by:

$$v_{obmSTO} = 1 - \frac{GOR}{GOR_0} \quad (5)$$

$$= \frac{GOR_0 - GOR}{GOR_0}$$

Equation (5) can be used for downhole oil based mud filtrate contamination monitoring in real time. Apparent gas/oil ratio can be measured by downhole fluid analysis at a series of time during cleanup. The endpoint, $GOR_0$ (gas/oil ratio for the native fluid), can be determined by the following different ways. Then the most suitable gas/oil ratio is selected for $GOR_0$.

GOR₀ from Density and Pressure Gradients

Figure 1:
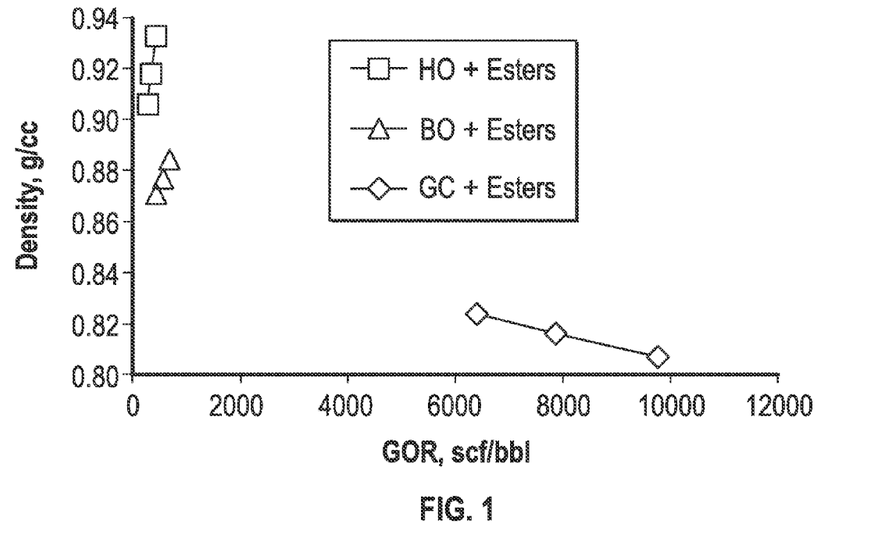
FIG. 1 is a density vs. gas/oil ratio for three (3) fluids.
Figure 2:
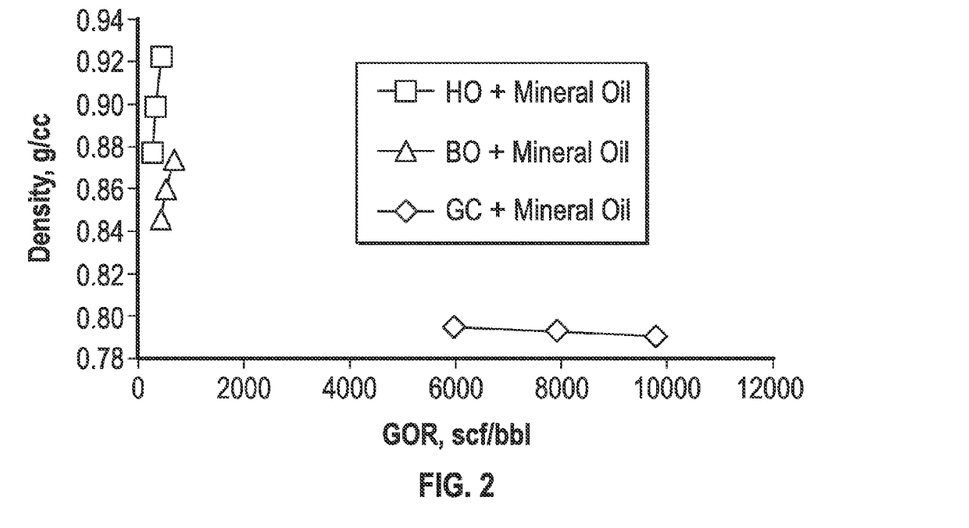
FIG. 2 is a density vs. gas/oil ratio for three (3) fluids.
Figure 3:
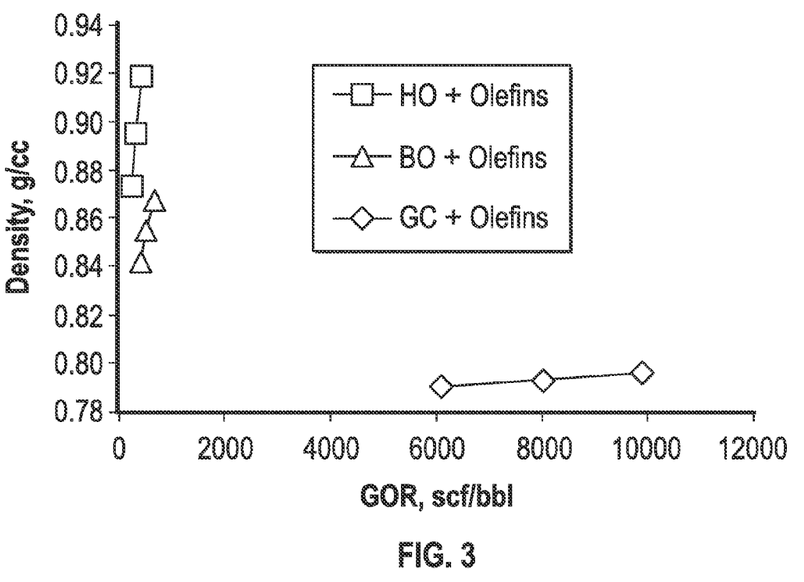
FIG. 3 is a density vs. gas/oil ratio for three (3) fluids.

Gas/oil ratio is typically in a linear relation with live fluid density. To test the relationship, gas condensate, black oil and heavy oil have been mixed with three types of oil based mud filtrates (esters, mineral oil and olefins) at 10 wt %, 25 wt % and 40 wt % oil based mud filtrate based on STO, respectively, and then the gas/ratio ratio and density are measured for all the mixtures. The results are shown in FIGS. 1, 2 and 3. The results clearly show that the relation between density and gas/oil ratio is linear.

Figure 4:
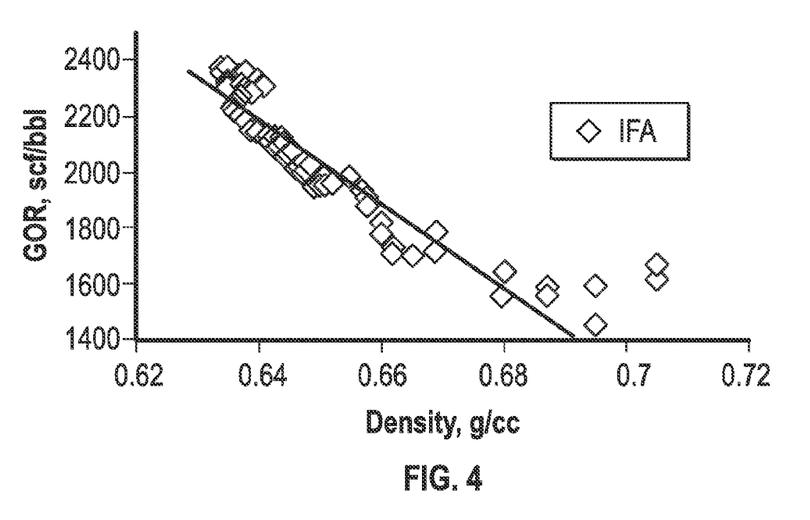
FIG. 4 is a graph of gas/oil ratio vs. live density.

The real time in situ fluid analyzer data also show the linear relationship between gas/oil ratio and live density as illustrated in FIG. 4. It can be seen that the higher density data in the low gas/oil ratio range are off the trend because the fluids may contain some solids and/or be compressed due to a pressure increase at the beginning of the cleanup process.

Because downhole fluid analysis measures apparent gas/oil ratio and density during cleanup, a linear relation can be determined from the cleanup data by selecting a suitable time interval. Pretest pressure (pressure gradient) data can be used to determine density of the contamination free fluid—density endpoint for the native fluid. Thus, the linear relation between gas/oil ratio and density can be extrapolated in terms of the density obtained from the pressure gradient. As a result, the endpoint $GOR_0$ can be determined. Once $GOR_0$ is obtained, oil based mud filtrate contamination level can be estimated by Equation (5) at a series of time (pumpout volume) based on apparent gas/oil ratio measured by downhole fluid analysis. On the other hand, this linear relation can be used to obtain the density of pure oil based mud filtrate by setting gas/oil ratio to zero.

$GOR_0$ from Density Regression and the Linear Relation Between GOR and Density

During cleanup, live fluid density can also be fitted by the following empirical expression:

$$\rho = \rho_0 - \beta V^{-\gamma} \quad (6)$$

where $\rho$ and $V$ are the density and pumpout volume (can be replaced by time t) measured by downhole fluid analysis; $\rho_0$, $\beta$ and $\gamma$ are three adjustable parameters. Once good density data regression is obtained, density ($\rho_0$) for the native fluid can be extrapolated by assuming that the pumpout volume (time) approaches infinity. Then $GOR_0$ for the native fluid can be determined from the linear relationship between gas/oil ratio and density mentioned previously. For the focused flow, V can be replaced by the volume in the sample line instead of total volume (summation of sample and guard line volumes).

$GOR_0$ and Density from Nearby Wells or/and Nearby Downhole Fluid Analysis Stations Both $GOR_0$ and density ($\rho_0$) for the native fluid can be obtained from data of nearby wells or/and nearby DFA stations in the same well.

$GOR_0$ from the Plot of Apparent GOR Vs. Pumpout Volume (Time) Data

When gas/oil ratio becomes unchanged (derivative of gas/oil ratio with respect to pumpout volume (time) is zero) even changing flowrate in guard or sampling flowline, that gas/oil ratio is taken as $GOR_0$. This method may be used in field practice for focused sampling and new developed probes and packers.

$GOR_0$ from Fitting to Apparent GOR vs. Pumpout Volume (Time) Data

During cleanup, apparent gas/oil ratio can also be fitted by:

$$GOR = GOR_0 - \beta V^{-\gamma} \quad (7)$$

$GOR_0$, $\beta$ and $\gamma$ are the three regression parameters and they are determined by fitting the GOR and pumpout volume (time) data during cleanup. Setting V to infinity, $GOR_0$ is assumed to be the GOR for the native fluid.

Equation (7) can be rearranged as $$\Delta GOR = GOR_0 - GOR = \beta V^{-\gamma} \quad (8)$$

Combining Equation (5) and Equation (8) the following is obtained:

$$v_{obmSTO} = \frac{GOR_0 - GOR}{GOR_0} \quad (9)$$

$$= \frac{\beta V^{-\gamma}}{GOR_0}$$

If it is assumed $GOR_0$ from the apparent gas/oil ratio vs. V (or t) plot, the result is:

$$\ln(v_{obmSTO}) = \ln\left(\frac{GOR_0 - GOR}{GOR_0}\right) \quad (10)$$

$$= \ln\left(\frac{\beta}{GOR_0}\right) - \gamma \ln V$$

Figure 5:
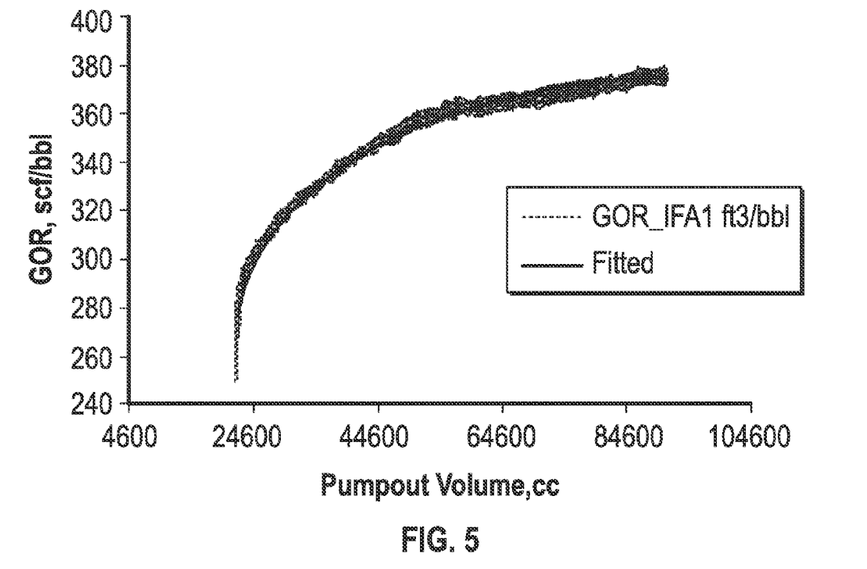
FIG. 5 is a gas/oil ratio fitting results using Equation (7).
Figure 6:
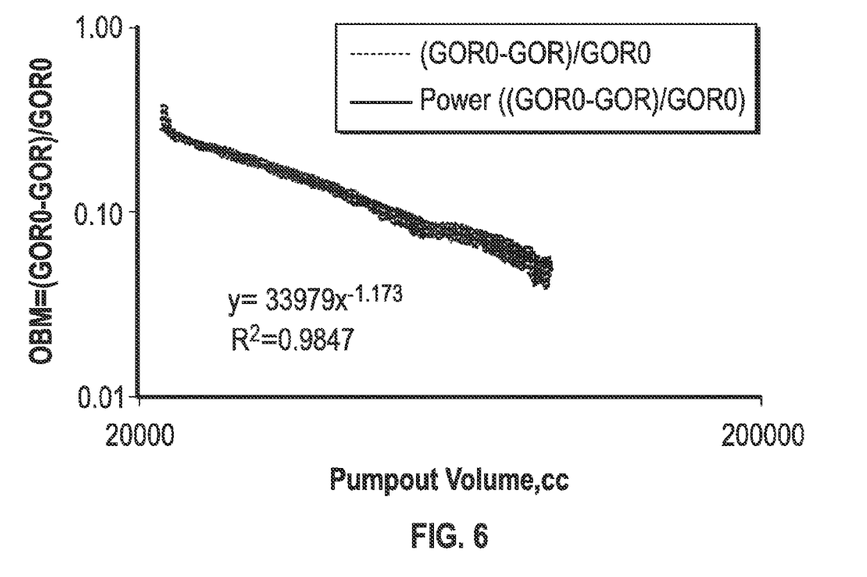
FIG. 6 is a plot of $\ln(v_{obmSTO})$ vs. $\ln(V)$.

A linear regression method may be used to obtain $\beta$ and $\gamma$. The constraints can be applied to the regression: $0 \leq \eta \leq 1$; $GOR \leq GOR_0$; $\frac{1}{3} \leq \gamma \leq 2$ ($\gamma$ constraint can be changed according to different packers and probes). In plots $\ln(v_{obmSTO})$ vs. $\ln(V)$ or $\ln(t)$. a straight line can be observed. The slope is $\gamma$ and the interception is $\ln(\beta/GOR_0)$. Because $GOR_0$ is assumed, $\beta$ can be determined. $GOR_0$ is then updated; updating $\beta$ and $\gamma$ is followed. The process may be repeated and the most suitable $GOR_0$ may be found for the best fit for the graph as well as other objectives. An example is shown in FIGS. 5 and 6 and the data come from in situ fluid analyzer measurements. FIG. 5 illustrates gas/oil ratio fitting results using Equation (7). FIG. 6 gives the $\ln(v_{obmSTO})$ vs. $\ln(V)$ plot. It can be seen that a nice linear relationship is observed.

All these methods can be used to obtain $GOR_0$ for the native fluid. Finally, a most suitable $GOR_0$ is selected for oil based mud filtrate contamination level estimation.

Once $GOR_0$ is obtained and the pumpout flowrate is known, the time required for sampling to reach a certain oil based mud level can be calculated by:

$$\Delta t = \frac{\Delta V}{Q_{pump}} \quad (11)$$

where $\Delta t$, $\Delta V$, and $Q_{pump}$ are the time required to reach a specified OBM level, the pumpout volume required to reach the specified OBM level, and the pumpout volume flowrate (assuming to be a constant).

Using Density as Oil Based Contamination Monitoring

Again, the contaminated fluid is divided into two components: the pure oil based mud and the native fluid. It is assumed that the mixing of the oil based mud filtrate and native fluid is ideal, i.e., producing no excess volume:

$$V^{mol} = x_{obm} V_{obm}^{mol} + (1 - x_{obm}) V_0^{mol} \quad (12)$$

where $V^{mol}$ and x are the molar volume and mole fraction. Subscripts obm and 0 represent the pure oil based mud filtrate and native fluid. The molar volume and mole fraction can be changed into density ($\rho$) and oil based mud filtrate volume fraction ($v_{obm}$) at downhole conditions by:

$$\rho = v_{obm} \rho_{obm} + (1 - v_{obm}) \rho_0 \quad (13)$$

Rearranging Equation (13), the oil based mud filtrate volume fraction is expressed as $$v_{obm} = \frac{\rho_0 - \rho}{\rho_0 - \rho_{obm}} \quad (14)$$

$v_{obm}$ can be related to the weight fraction of oil based mud contamination at downhole conditions by:

$$w_{obm} = \frac{v_{obm} \rho_{obm}}{\rho} \quad (15)$$

$$= \frac{\rho_{obm}(\rho_0 - \rho)}{\rho(\rho_0 - \rho_{obm})}$$

In Equation (14) and Equation 15, two endpoints—densities of pure oil based mud ($\rho_{obm}$) and native fluid ($\rho_0$) should be known. It should be noted that density contrast between the pure oil based mud filtrate and native fluid should be large enough in order to use Equation (14) and (5) for oil based mud filtrate contamination monitoring.

Determination of Density of Pure OBM ($\rho_{obm}$)

The density of pure oil based mud filtrate can be determined
 a) Measure the density of pure oil based mud filtrate if pure oil based mud filtrate (or base oil) is available before logging at different temperatures and pressures covering entire reservoir conditions.
 b) According to the linear relationship between gas/oil ratio and density mentioned previously, setting gas/oil ratio to zero, the density obtained is the density of the pure oil based mud filtrate.
 c) At the beginning of clearup, 100% oil based mud filtrate may be pumped in flowline. The downhole fluid analysis measured density at the beginning of clearup may be considered to be the density of pure oil based mud filtrate.

Determination of Density of Native Fluid ($\rho_0$)

The density of native fluid can be determined as follows:
 d) Pretest pressure (pressure gradient) data can be used to determine density of the contamination free fluid—density endpoint for the native fluid.
 e) During cleanup, live fluid density can also be fitted by Equation (6). Once good density data regression is obtained, density ($\rho_0$) for the native fluid can be extrapolated when the pumpout volume (time) approaches infinity.

Once the two endpoint densities are obtained, Equation (14) and (15) are used to estimate oil based mud filtrate contamination level.

Figure 7:
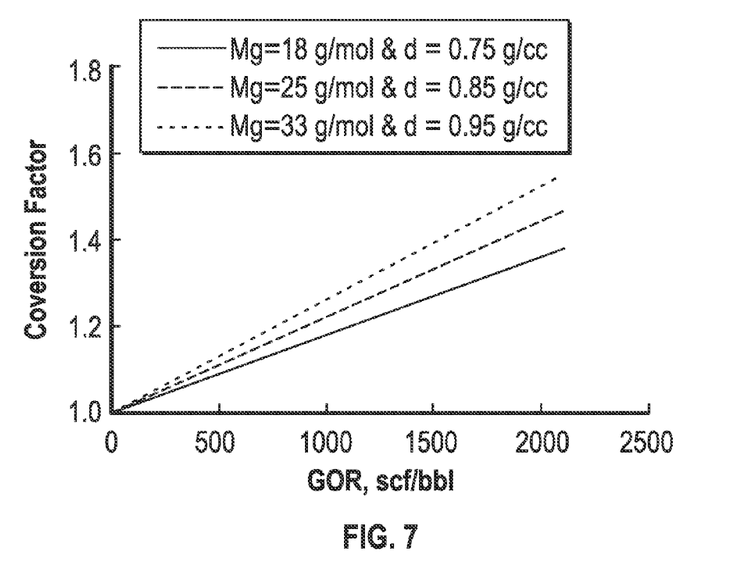
FIG. 7 is a plot showing a conversion factor as a function of gas/oil ratio, $M_{gas}$ and $\rho_{STOStd}$

Oil based mud contamination level in weight fraction can be converted between standard and downhole conditions by Equation 16 below:

$$\frac{w_{obmSTO}}{w_{obm}} = \left(1 + GOR\frac{M_{gas}P_{Std}}{\rho_{STOStd}RT_{Std}}\right) \quad (16)$$

$$= \text{conversion factor}$$

where $w_{obmSTO}$, $\rho_{STOStd}$, $M_{gas}$, R, $P_{Std}$ and $T_{Std}$ are the oil based mud filtrate contamination level in weight fraction based on STO at standard conditions, the STO density at standard conditions, the molecular weight of flashed gas at standard conditions, the universal gas constant, the standard pressure (typically 14.7 psia) and standard temperature (typically 60° F.), respectively. $\rho_{STOStd}$ and $M_{gas}$ can be estimated by the method proposed in U.S. Pat. No. 7,920,970. FIG. 7 shows the conversion factor as a function of gas/oil ratio, $M_{gas}$ and $\rho_{STOStd}$. For high gas/oil ratio fluids, oil based mud weight fraction based on STO is quite different from that at downhole conditions.

Oil based mud contamination level in volume fraction is then converted between standard and downhole conditions by Equation 17 below:

$$\frac{v_{obmSTO}}{v_{obm}} = \left(\frac{\rho_{obm}}{\rho_{obmStd}}\right)\left(\frac{\rho_{STOStd}}{\rho}\right)\left(1 + GOR\frac{M_{gas}P_{Std}}{\rho_{STOStd}RT_{Std}}\right) \quad (17)$$

$$= \left(\frac{\rho_{obm}}{\rho_{obmStd}}\right)B_o$$

where $B_o$ is the formation volume factor of the contaminated fluid.

If it is assumed that the density ratio of oil based mud filtrate to fluid at reservoir and standard conditions (i.e., the isothermal compressibility of both oil based mud filtrate and fluid) are approximately identical, the same conversion factor can be used for both oil based mud weight and volume fractions.

The existing oil based mud filtrate contamination monitoring methods such as the methane and color channel oil based mud filtrate contamination algorithms, multi-channel oil based mud filtrate contamination algorithms can be used as well.

Figure 8:
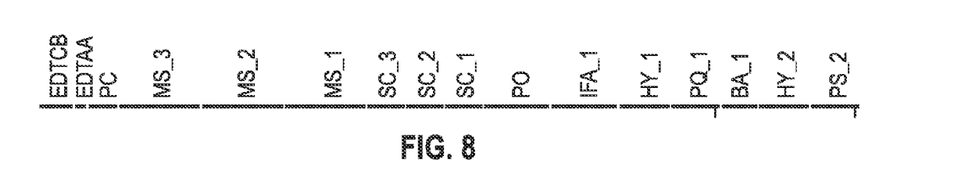
FIG. 8 is a tool string using the methodology disclosed.
Figure 9:
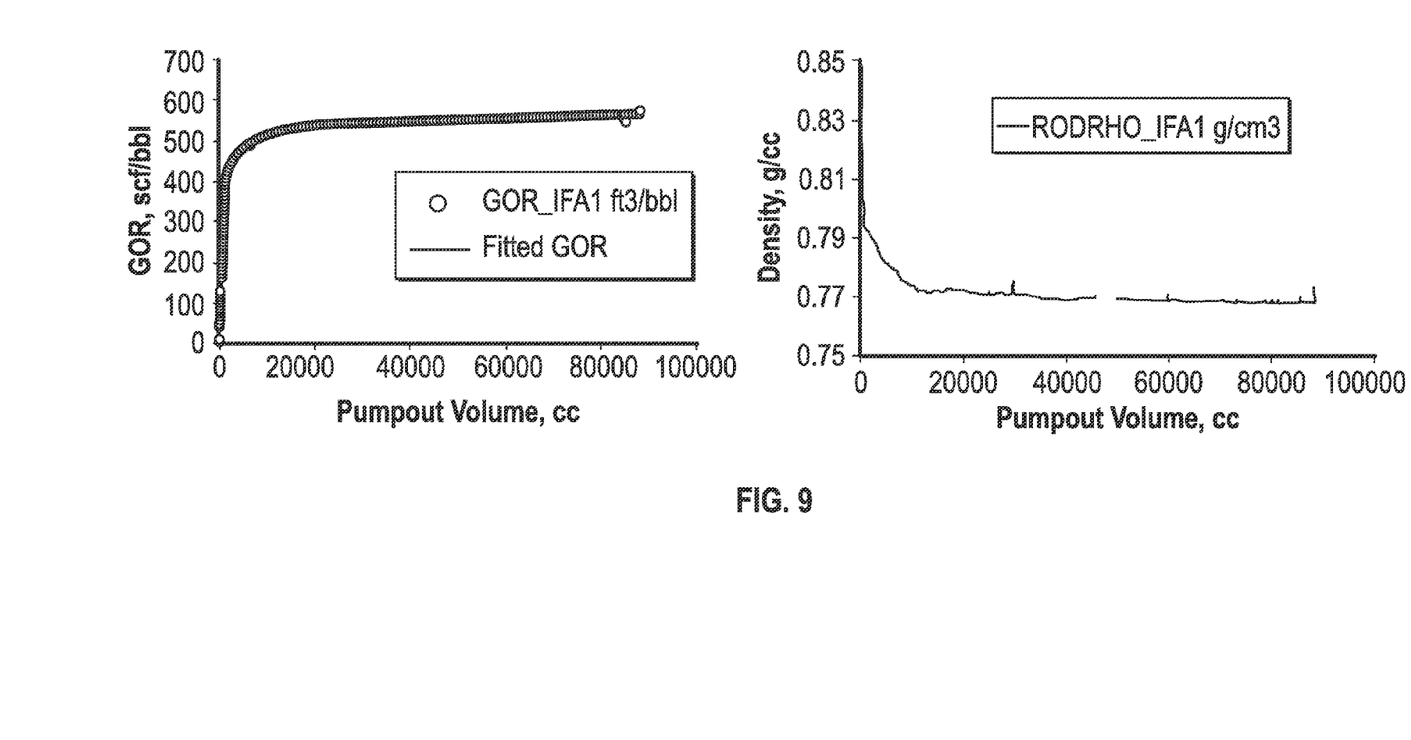
FIG. 9 is a plot of gas/oil ratio and density variations with pumpout volume.
Figure 10:
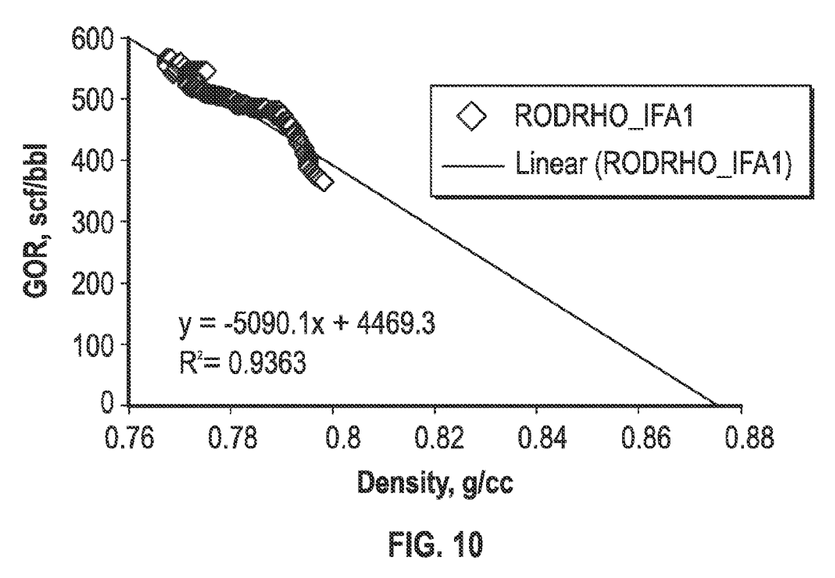
FIG. 10 is plot of gas/oil ratio and density relationship.
Figure 11:
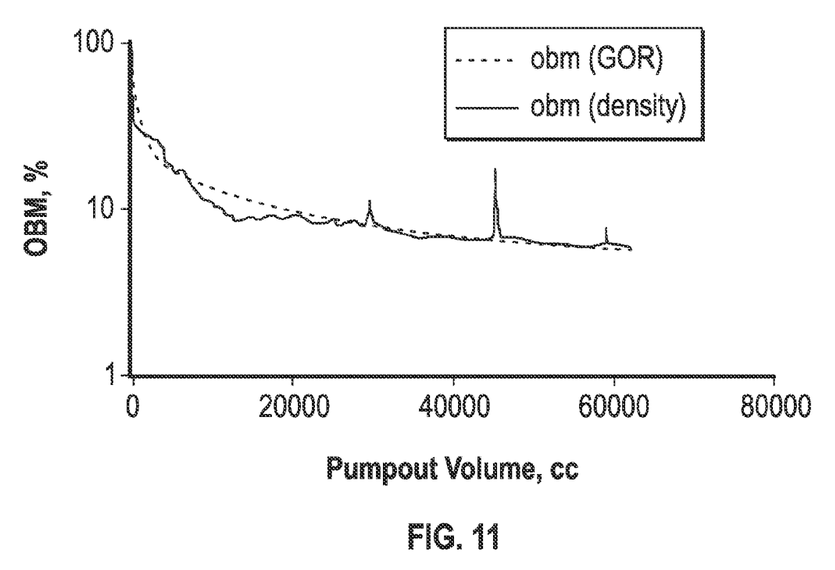
FIG. 11 is plot wherein oil based mud level can be obtained by both gas/oil ratio and density values.

An example is given below:
The tool string is shown in FIG. 8. The PQ, DV-Rod and in situ fluid analysis were used. Only comingling up flow was performed. Gas/oil ratio and density variations with pumpout volume are shown in FIG. 9. The gas/oil ratio and density relationship is given in FIG. 10. GOR fitting (FIG. 9) shows $GOR_0$=595 scf/bbl for the native oil. The native oil and pure OBM densities are obtained by the linear relation between GOR and density, $\rho_0$=0.762 g/cm3 and $\rho_{obm}$=0.875 g/cm3. Therefore, the oil based mud filtrate contamination level can be obtained by both gas/oil ratio and density as shown in FIG. 11. They are very close.

While the aspects has been described with respect to a limited number of embodiments, those skilled in the art, having benefit of this disclosure, will appreciate that other embodiments can be devised which do not depart from the scope of the disclosure herein.

What is claimed is:

1. A method for monitoring oil based mud filtrate contamination, comprising:
    analytically dividing a fluid stream into two parts;
    determining a gas/oil ratio for a native fluid;
    determining an apparent gas/oil ratio for the contaminated fluid; and
    determining on a volume fraction at downhole conditions, an oil based mud filtrate contamination level based upon the gas/oil ratio for the native fluid, the apparent gas/oil ratio for the contaminated fluid, and a formation volume factor of the contaminated fluid.

2. The method according to claim 1, wherein the gas/oil ratio is measured using optical density analysis.

3. The method according to claim 1, wherein a single packer is used to determine the gas/oil ratio for the native fluid.

4. The method according to claim 1, further comprising: estimating an endpoint gas/oil ratio for native oil from data from at least one nearby well.

5. The method according to claim 1, wherein the gas/oil ratio is determined from a live fluid density.

6. The method according to claim 5, wherein the live fluid density is obtained from pressure gradients.

7. The method according to claim 5, wherein the live fluid density is obtained during a cleanup process.

8. The method according to claim 1, wherein the apparent gas/oil ratio is calculated by curve fitting.

9. The method according to claim 8, wherein the curve fitting is performed through a formula:

$$GOR = GOR_0 - \beta V^{-\gamma}.$$

10. The method according to claim 1, further comprising: determining an endpoint gas/oil ratio.

11. The method according to claim 10, wherein the endpoint gas/oil ratio is determined through an analysis of live fluid density.

12. The method according to claim 10, further comprising:
analyzing a live fluid density regression to determine the endpoint gas/oil ratio.

13. A method for monitoring oil based mud filtrate contamination in a downhole environment, comprising:
lowering a downhole device into the downhole environment;
sampling a fluid from the downhole environment;
analytically dividing the fluid into two parts, an oil based mud and a native fluid;
determining a gas/oil ratio for the native fluid;
determining an apparent gas/oil ratio for the contaminated fluid; and
determining on a volume fraction at downhole conditions, an oil based mud filtrate contamination level based upon the gas/oil ratio for the native fluid, the apparent gas/oil ratio for the contaminated fluid, and a formation volume factor of the contaminated fluid.

14. The method according to claim 13, further comprising:
determining an endpoint gas/oil ratio for the native fluid.

15. The method according to claim 14, wherein the endpoint gas/oil ratio for the native fluid is determined through an analysis of live fluid density.

16. The method according to claim 14, further comprising:
analyzing a live fluid density regression to determine the endpoint gas/oil ratio.

* * * * *